United States Patent
Chow et al.

(10) Patent No.: US 7,294,187 B2
(45) Date of Patent: Nov. 13, 2007

(54) RAPID-HARDENING CALCIUM PHOSPHATE CEMENT COMPOSITIONS

(75) Inventors: Laurence C. Chow, Germantown, MD (US); Shozo Takagi, Gaithersburg, MD (US)

(73) Assignee: ADA Foundation, Chicago, IL (US)

(*) Notice: Subject to any disclaimer, the term of this patent is extended or adjusted under 35 U.S.C. 154(b) by 141 days.

(21) Appl. No.: 10/941,443

(22) Filed: Sep. 15, 2004

(65) Prior Publication Data
US 2005/0074415 A1    Apr. 7, 2005

Related U.S. Application Data

(63) Continuation-in-part of application No. 10/057,554, filed on Jan. 23, 2002, now Pat. No. 6,793,725.

(60) Provisional application No. 60/536,899, filed on Jan. 16, 2004, provisional application No. 60/263,894, filed on Jan. 24, 2001.

(51) Int. Cl.
*A61L 27/12* (2006.01)
*A61L 27/58* (2006.01)

(52) U.S. Cl. .................. 106/35; 106/690; 106/691; 623/23.62; 623/23.61

(58) Field of Classification Search ............ 623/23.62, 623/23.61; 106/35, 690, 69
See application file for complete search history.

(56) References Cited

U.S. PATENT DOCUMENTS

| | | |
|---|---|---|
| 3,679,360 A | 7/1972 | Rubin et al. |
| 3,787,900 A | 1/1974 | McGee |
| 3,913,229 A | 10/1975 | Driskell et al. |
| 3,929,971 A | 12/1975 | Roy |
| 4,097,935 A | 7/1978 | Jarcho |
| 4,497,075 A | 2/1985 | Niwa et al. |
| 4,512,038 A | 4/1985 | Alexander et al. |
| 4,518,430 A * | 5/1985 | Brown et al. ............. 106/35 |
| 4,599,085 A | 7/1986 | Riess et al. |
| 4,612,053 A | 9/1986 | Brown et al. |
| 4,655,777 A | 4/1987 | Dunn et al. |
| 4,880,610 A | 11/1989 | Constantz et al. |
| 4,897,250 A | 1/1990 | Sumita |
| RE33,161 E * | 2/1990 | Brown et al. ............. 423/308 |

(Continued)

FOREIGN PATENT DOCUMENTS

DE       4016135 A1   11/1990

(Continued)

OTHER PUBLICATIONS

Briner, et al., "Significance of Enamel Remineralization", *J. Dent. Res.* 53:239-243 (1974).

(Continued)

*Primary Examiner*—C. Melissa Koslow
(74) *Attorney, Agent, or Firm*—Banner & Witcoff, Ltd.

(57) ABSTRACT

A bone or dental implant material in the form of a paste includes a mixture of calcium phosphate and/or calcium-containing powders and a solution that is (1) an acidic calcium phosphate solution saturated with respect to one or more calcium phosphate compounds, (2) a concentrated acid solution, or (3) salt solutions with a cationic component other than calcium. The paste is stable, resistant to washout and will form hydroxyapatite and harden relatively rapidly to a cement.

16 Claims, 2 Drawing Sheets

U.S. PATENT DOCUMENTS

| | | | |
|---|---|---|---|
| RE33,221 E * | 5/1990 | Brown et al. | 423/308 |
| 4,959,104 A * | 9/1990 | Iino et al. | 106/691 |
| 4,963,151 A | 10/1990 | Ducheyne et al. | |
| 5,034,059 A | 7/1991 | Constantz et al. | |
| 5,037,639 A | 8/1991 | Tung | |
| 5,047,031 A | 9/1991 | Constantz et al. | |
| 5,053,212 A | 10/1991 | Constantz et al. | |
| 5,092,888 A | 3/1992 | Iwamoto et al. | |
| 5,129,905 A | 7/1992 | Constantz et al. | |
| 5,152,836 A * | 10/1992 | Hirano et al. | 106/690 |
| 5,181,930 A | 1/1993 | Dumbleton et al. | |
| 5,192,330 A | 3/1993 | Chang et al. | |
| 5,238,491 A | 8/1993 | Sugihara et al. | |
| 5,336,264 A | 8/1994 | Constanz et al. | |
| 5,455,231 A | 10/1995 | Constantz et al. | |
| 5,496,399 A | 3/1996 | Ison et al. | |
| 5,522,893 A | 6/1996 | Chow et al. | |
| 5,525,148 A * | 6/1996 | Chow et al. | 106/35 |
| 5,542,973 A | 8/1996 | Chow et al. | |
| 5,545,254 A | 8/1996 | Chow et al. | |
| 5,556,687 A | 9/1996 | McMillin | |
| 5,652,056 A | 7/1997 | Pepin | |
| 5,695,729 A | 12/1997 | Chow et al. | |
| 5,721,049 A | 2/1998 | Marcolongo et al. | |
| 5,766,618 A | 6/1998 | Laurencin et al. | |
| 5,968,253 A | 10/1999 | Poser | |
| 5,976,234 A | 11/1999 | Chow et al. | |
| 5,997,624 A | 12/1999 | Chow et al. | |
| 6,077,989 A | 6/2000 | Kandel et al. | |
| 6,136,029 A | 10/2000 | Johnson et al. | |
| 6,207,098 B1 | 3/2001 | Nakanishi et al. | |
| 6,214,008 B1 | 4/2001 | Illi | |
| 6,281,256 B1 | 8/2001 | Harris et al. | |
| 6,281,257 B1 | 8/2001 | Ma et al. | |
| 6,287,341 B1 | 9/2001 | Lee et al. | |
| 6,325,992 B1 | 12/2001 | Chow et al. | |
| 6,425,949 B1 | 7/2002 | Lemaitre | |

FOREIGN PATENT DOCUMENTS

| | | | |
|---|---|---|---|
| EP | 0416761 A1 | 3/1991 | |
| EP | 0520 690 A2 | 12/1992 | |
| JP | 62275007 A | 11/1987 | |
| JP | 1029266 A | 1/1989 | |
| JP | 1301543 A | 12/1989 | |
| JP | 3183605 A | 8/1991 | |
| JP | 31936159 | 8/1991 | |
| JP | 4059611 A2 | 5/2007 | |
| WO | WO95/03369 | 2/1995 | |
| WO | WO 9503369 | 2/1995 | |

OTHER PUBLICATIONS

Silverstone, "Remineralization Phenomena", *Caries Res.* 11 (Supp. 1): 59-84 (1977).

Brown, Solubilities of Phosphates and Other Sparingly Soluble Compounds, from Griffith, et al., *Environmental Phosphorous Handbook* (John Wiley & Sons, New York 1973).

Miyazaki, et al., "An Infrared Spectroscopic Study of Cement Formation of Polymeric Calcium Phosphate Cement," *Journal of Japanese Society for Dental Materials and Devices*, vol. II, No. 2, 1992.

(1965 Brown, et al., "Crystallography of Tetracalcium Phosphate," *J. Res. Nat. Bur. Stands.* 69A: 547-551).

Driskell, et al., "Development of Ceramic and Ceramic Composite Devices for Maxillofacial Application", *J. Biomed. Mat. Res.* 6: 345-361 (1972).

Gelhard et al, "Rehardening of Artificial Enamel Lesions in Vivo", *Caries Res.* 13: 80-83 (1979).

Gregory, et. al., "Solubility of $CaHPO_4 2H_2O$ in the System $Ca(OH)_2$—$H_3PO_4$-$H_2O$ at 5, 15, 25, and 37.5° C.," *J. Res. Nat. Bur. Stand.* 74A: 461-475 (1970).

Gregory, et al., "Solubility of—$Ca_3(PO_4)_2$ in the System $Ca(OH)_2$—$H_3PO_4$—$H_2O$ at 5, 15, 25 and 37° C.," *J. Res. Nat. Bur. Stand*, 78A: 667-674 (1974).

Hiatt, et al., "Root Preparation I. Obturation of Dentinal Tubules in Treatment of Root Hypersensitivity", *J. Periodontal* 43: 373-380 (1972).

McDowell, et al., "Solubility of—$Ca_5(PO_4)_3$ in the System $Ca(OH)_2$—$H_3PO_4$—$H_2O$ at 5, 15, 25 and 37° C.," *J. Res. Nat. Bur. Stand*, 81A:273-281 (1977).

McDowell, et al., "Solubility Study of Calcium Hydrogen Phosphate. Ion Pair Formation," *Inorg. Chem*, 10:1638-1643 (1971).

Moreno, et al., "Stability of Dicalcium Phosphate Dihydrate in Aqueous Solutions and Solubility of Octacalcium Phosphate," *Soil Sci. Soc. Am. Proc.* 21: 99-102 (1960).

Patel, et al., "Solubility of $CaHPO_4$ $2H_2O$ in the Quaternary System $Ca(OH)_2$—$H_3PO_4$—$NaCl$—$H_2O$ at 25° C.," *J. Res. Nat. Bur. Stands*. 78A: 675-681 (1974).

Pickel, et al. "The Effect of a Chewing Gum Containing Dicalcium Phosphate on Salivary Calcium and Phosphate", *Ala. J. Med. Sci.* 2: 286-287.

*Guide to Dental Materials and Devices*, 7th Ed. (ADA 1974) pp. 49-64.

Brown, et al., (1988): "A New Calcium Phosphate, Water Setting Cement," *Cements Research Progress* 1986, P.W. Brown, Ed., Westerville, Ohio: American Ceramic Society, pp. 352-379.

Chohayeb, A.A., et al., (1987): Evaluation of Calcium Phosphate as a Root Canal Sealer-Filler Material, *J. Endod* 13, 384-386.

Hong, et al., (1989): The Periapical Tissue Reactions to a Calcium Phosphate Cement in the Teeth of Monkeys, *J. Dent Res* (submitted).

Constantino, et al. (1989): Evaluation of a New Hydroxyapatite Cement: Cranioplasty in a Cat Model, The Fith International Symposium on Facial Plastic Reconstructive Surgery of the Head and Neck, Toronto, Canada.

De Rijk, et al. (1986): Clinical Evaluation of an Hydroxyapatite Precipitate for the Treatment of Dentinal Hypersensitivity, *Biomedical Engineering V. Recent Developments*, Proc of 5th Southern Biomedical Engineering Conference, Subrata Saha, Ed., New York: Pergamon Press, pp. 336-339.

Grunninger et al, (1984): Evaluation of the Biocompatibility of a New Calcium Phosphate Setting Cement, *J. Dent Res.*, 63 (Special Issue) Abst. No. 270.

Sugawara, et. al, (1987): A Calcium Phosphate Root Canal Sealer-Filler, *J. Dent Res.* 66: 296 Abst. No. 1516.

Sugawara et al (1989): Formation of Hydroxyapatite in Hydrogels from Tetracalcium Phosphate/Dicalcium Phosphate Mixtures, *Nihon Univ. Sch. Dent.*, vol. 31, No. 1, 372-81, 1989.

Block, et al. (1988): Correction of Vertical Orbital Dystopia with a Hydroxyapatite Orbital Floor Graft, *J. Oral Maxillofac Surg* 46: 420-425, 1988.

Salyer, et al. (1989): Porous Hydroxyapatite as an Onlay Bone-Graft Substitute for Maxillofacial Surgery, *Plas and Recon Surg* 84, 2:236-244, 1989.

Kenney, et al. (1988): The Use of a Porous Hydroxyapatite Implant in Peridontal Defects, *J. Periodontal*, pp. 67-72 Feb. 1988.

Zide et al (1987): Hydroxyapatite Cranioplasty Directly Over Dura, *J. Oral Maxillofac Surg* 45:481-486, 1987.

Waite, et al. (1986): Zygomatic Augmentation with Hydroxyapatite, *J. Oral Maxillofac Surg* 44:349-352, 1986.

Grote, (1984): Tympanoplasty With Calcium Phosphate, *Arch Otolaryngology* 110:197-199, 1984.

Kent, et al. (1983): Alveolar Ridge Augmentation Using Nonresorbable Hydroxyapatite With or Without Autogenous Cancellous Bone, *J. Oral Maxillofac Surg* 41:629-642, 1983.

Piecuch (1986): Augmentation of the Atrophic Edentulous Ridge with Porous Replamineform Hydroxyapatite (Interpore-200), *Dental Clinics of North America* 30, 2:291-305, 1986.

Misch (1987): Maxillary Sinus Augmentation for Endosteal Implants: Organized Alternative Treatment Plans, *Int J Oral Implant* 4, 2:49-58, 1987.

Chow, L.C., "Calcium Phosphate Materials: Reactor Response" *Adv Dent Res* 2(1): 191-184, Aug. 1988.

Fukase, et al., "Setting Reactions and Compressive Strengths of Calcium Phosphate Cements", *J Dent Res* 69(12):1852-1856, Dec. 1990.

Chow, et al., "Self-Setting Calcium Phosphate Cements," Mat. Res. Soc. Symp. Proc. vol. 179, 1991.

Miyazaki, et al. "Chemical Change of Hardened PCA/CPC Cements in Various Storing Solutions," *The Journal of the Japanese Soc. for Den. Mats. and Devices*, vol. 11, No. 2, 1992.

Fukase et al, "Thermal Conductivity of Calcium Phosphate Cement," IADR Abstract, 1990.

Sugawara, et al., "An In Vitro Study of Dentin Hypersensitivity Using Calcium Phosphate Cement," *Jour of Jap. Soc. for Dent. Mats & Devices*, vol. 8, No. 2 1989.

Constantino, et al., "Hydroxyapatite Cement—Basic Chemistry and Histologic Properties," *Arch. of Otolaryngology—Head & Neck Surgery*, vol. 117, pp. 379-384 (Apr. 1991).

Friedman, et al., "Hydroxyapatite Cement—Obliteration and Reconstruction of the Cat Frontal Sinus," *Arch. of Otolaryngology—Head & Neck Surgery*, vol. 117, pp. 385-389 (Apr. 1991).

Mirtchi, et al., "Calcium phosphate cements: study of the β-tricalcium phosphate-monocalcium phosphate system," *Biomaterials*, vol. 10, pp. 475-480 (1989).

Mirtchi, et al., "Calcium phosphate cements: study of the β-tricalcium phosphate-dicalcium phosphate-calcite cements," *Biomaterials*, vol. 11, pp. 83-88 (1990).

Mirtchi, et al., "Calcium phosphate cements: effect of fluorides on the setting and hardening of β-tricalcium phosphate-dicalcium phosphate-calcite cements," *Biomaterials*, vol. 12, pp. 505-510 (1991).

Fulmer, et al. "Effects of $Na_2 HPO_4$ and $NaH_2PO_4$ on Hydroxyapatite Formation," *J. Biomed. Mat. Res.*, vol. 27, pp. 1095-1102 (1993).

Ishikawa, et al., "The Hydrolysis of Anhydrous Dicalcium Phosphate into Hydroxyapatite," *J. of Dent. Res.*, vol. 72, No. 2, pp. 474-480 (Feb. 1993).

Sugawara, et al., "In Vitro Evaluation of the Sealing Ability of a Calcium Phosphate Cement When Used 5s a Root Canal Sealer-Filler," *J. of Endodontics*, vol. 16, No. 4, pp. 162-165 (1990).

Shindo, et al., "Facial Skeletal Augmentation Using Hydroxyapatite Cement," *Arch. of Otolaryngology—Head & Neck Surgery*, vol. 119, pp. 185-190 (Feb. 1993).

Constantino, et al., "Experimental Hydroxyapatite Cement Cranioplasty," *Plastic and Reconstructive Surgery*, vol. 90 No. 2, pp. 174-185 (Aug. 1992).

Sanin, et al., K. Ishikawa, S. Takagi, L.C. Chow and E.D. Eanes, "*Effects of Additives on Setting Reaction of Calcium Phosphate Cement*," IADR Abstr. #666 J. Dent Res. 71 189 (1992).

Driessens, et al., 1993, "New Apatite Calcium Phosphate Bone Cement: Preliminary Results," in Bioceramics (Ducheyne & Christiansen, eds.) Butterworth-Heinemann Ltd., vol. 6, pp. 469-473.

Miyazaki, et al., 1993, "Polymeric calcium phospae cements: analysis of reaction products and properties," Dent.Mater. 9:41-45.

Miyazaki et al, 1993, "Polymeric calcium phosphate cements: setting reaction modifiers," Dent Mater. 9:46-50.

Chow et al., 1994, "Formulation of Hydroxyapatite in Cement Systems," in *Hydroxyapatite and Related Materials* (Brown & Constanz, eds.), CRC Press: Boca Raton, FL pp. 127-137.

Constantz, et al., 1995, "Skeletal Repair by Situ Formation of the Mineral Phase of Bone," Science 267:1796-1798.

Chow and Takagi, 1995, "Rate of Dissolution of Calcium Phosphate Cements," J. Dent. Res. 74:537(IADR Abstract #1094).

Takagi and Chow, 1995, "Formation of Macropores in Calcium Phosphate Cement Implants," J. Dent. Res. 74:537 (IADR Abstract # 1272).

Horioglu, et al., 1995, "Composite Implant of Hydroxyapatite Cement/Osteogenic Protein-1 In Experimental Cranial Construction: Preliminary Results," Transactions of the 21st Annual Meeting for the Society for Biomaterials, San Francisco, CA, Mar. 18-22, p. 72.

Driessens, et al., 1995, "Effective formulations for the preparation of calcium phosphate bone cements," J. Mater.Sci.:Mater.Med. 5:164-170.

Fernandez, et al., 1994, "Common Ion Effect on some Calcium Phosphate Cements," Clinial Mater.16:99-103.

Matsuya, et al., 1994, Formation of Hydroxyapatitein a Polymeric Calcium Phosphate Cement, Proc. Int. Conf. Comp. Eng.

Bermudez, et al., Optimization of Calcium Orthophosphae Cement formulation occurring in the combination o monocalcium phosphate monohydrate with calcium oxide, J. Mater.SciMater Med 5:67-71.

Dickens-Venz, et. al., 1994, Physical and chemical properties of resin-reinforced calcium phosphate cements, Dent. Mater. 10:100-106.

"NASA and Dentistry" (1977).

Chow, "Development of Self-Setting Calcium Phosphate Cements," Journal of the Ceramic Society of Japan 99[10] 954-964 (1991).

Sugawara, et al., "Biocompatibility and Osteoconductivity of Calcium Phosphate Cement" IADR Abstract (1990).

Miyazaki et al., "Polymeric Calcium Phosphate Cements", IADR Abstract (1990).

Sugawara et al., "Histopathological Reactions of a Calcium Phosphate Cement Root Canal Filler", IADR Abstract (1991).

Sanin et al., "Particle Size Effects on pH and Strength of Calcium Phosphate Cement", IADR Abstract (1991).

Link et al., "Composite of Calcium Phosphate Cement and Genetically Engineered Protein Bioadhesive", IADR Abstract (1991).

Matsuya et al., "Effects of pH on the Reactions of Tetracalcium Phosphate and Dicalcium Phosphate", IADR Abstract (1991).

Chow et al., "X-ray Diffraction and Electron Microscopic Characterization of Calcium Phosphate Cement Setting Reactions", IADR Abstract (1987).

Sugawara et al., "An In Vitro Study of Dentin Hypersensitivity Using Calcium Phosphate Cement", Jour of Jap. Soc. For Dent. Mats & Devices, vol. 8, No. 2, 1989.

Mirtchi et al., "Calcium Phosphate Cements: Action of Setting Regulars on the Properties of the β-tricalcium Phosphate-Monocalcium Phosphate Cements" *Biomaterials*, vol. 10, pp. 634-638 (1989).

Cherng et al., 1995, Effects of Gelling Agents on Calcium Phosphate Cements, *J. Dent. Res.* 74:242 (IADR Abstract, No. 1845).

Horioglu et al., 1995, "Long-Term Follow-Up of Hydroxyapatite Cement (HAC) Implant for Craniofacial Construction", *Transactions of the 21st Annual Meeting for the Society of Biomaterials*, San Francisco, CA, Mar. 18-22, p. 198.

Fujikawa et al., 1995, "Histopathological Reaction of Calcium Phosphate Cement in Periodontal Bone Defect", *Dent. Mater. J.* 10:45-57.

Shors et al., "Porous Hydroxyapatite", *An Introduction to Bioceramics*, pp. 181-198.

Fukase et al., "Setting Reactions and Compressive Strengths of Calcium Phosphate Cements", *J. Dent. Res* 69 (12): 1852, Dec. 1990.

Matsuya et al., Effect of Fluoride on Apatite Formation From $Ca_4(PO_4)_2O$ in 0.1 mol $L^{-1}$ $KH_2PO_4$, *J Mat. Sci Materials in Medicine* 9 (1998) pp. 325-331.

Chang et al., "Osteoconduction at Porous Hydroxyapatite with Various Pore Configurations", *Biomaterials* 21 (2000) 1291-1298.

Chow et al., "Calcium Phosphate Cements", *Cements Research Progress*, 1999, pp. 215-238.

Xu et al., "Calcium Phosphate Cement Containing Resorbable Fibers for Short-Term Reinforcement and Macroporosity", *Biomaterials* 0 (2001) 1-10.

Xu et al., "Strong and Macroporous Calcium Phosphate Cement: Effects of Porosity and Fiber Reinforcement on Mechanical Properties", *Macroporous Calcium Phosphate Cement*, pp. 1-10.

Chow, "Calcium Phosphate Cements: Chemistry, Properties and Applications", *Mat. Res. Soc. Sump. Proc.*, vol. 599, 2000.

Takagi et al., Formation of Macropores in Calcium Phosphate Cement Implants, *J. Mat. Sci: Materials in Medicine*, 12 (2001) 135-139.

Von Gonten et al., "Load-Bearing Behavior of a Simulated Craniofacial Structure Fabricated From a Hydroxyapatite Cement and Bioresorbable Fiber-Mesh" *J. Mater. Sci.: Materials in Medicine*, 11 (2000) 95-100.

Xu et al., "Effects of Fiber Length and Volume Fraction on the Reinforcement of Calcium Phosphate Cement" *J. Mater. Sci: Materials in Medicine*, 12 (2001) 57-65.

Xu et al., "Reinforcement of a Self-Setting Calcium Phosphate Cement with Different Fiber", *Journal o Biomedical Materials Research*, Oct. 2000, vol. 51, No. 1, pp. 107-114.

Suchanek et al., "Processing and Properties of Hydroxyapatite-Based Biomaterials for use as Hard Tissue Replacement Implants", *J. Mater. Res.*, vol. 13, No. 1, Jan. 1998, pp. 94-117.

Simske, et al., "Porous Materials for Bone Engineering", *Materials Science Forum*, vol. 250 (1997) pp. 151-182.

LeGeros, "Biodegradation and Bioresorption of Calcium Phosphate Ceramics", *Clincial Materials*, 14 (1993) pp. 65-88.

Friedman et al., "BoneSource Hydroxyapatite Cement: A Novel Biomaterial for Craniofacial Skeletal Tissue Engineering and Reconstruction", *Hac For Tissue Engineering and Reconstruction*, pp. 428-432.

Takagi et al., "Morphological and Phase Characterizations of Retrieved Calcium Phosphate Cement Implants", 2000, pp. 36-41.

Ishikawa et al., "Reaction of Calcium Phosphate Cements With Different Amounts of Tetracalcium Phosphate and Dicalcium Phosphate Anhydrous", *CPC With Different TTCP/DCPA Molar Ratios*, pp. 504-510.

Miyamoto et al., "Histological and Compositional Evaluations of Three Types of Calcium Phosphate Cements When Implanting in Subcutaneous Tissue Immediately After Mixing", *Three CPCs in Soft Tissue*, 1999, pp. 36-42.

Constantz et al., "Histological, Chemical, and Crystallographic Analysis of Four Calcium Phosphate Cements in Different Rabbit Osseous Sites", *Calcium Phosphate Cements*, 1998, pp. 451-461.

Ginebra et al., "Setting Reaction and Hardening of an Apatitic Calcium Phosphate Cement", *J. Dent. Res.*, 76 (4): 905-912, Apr. 1997.

Blumenthal, et al., "Effect of Preparation Conditions on the Properties and Transformation of Amorphous Calcium Phosphate", *Mat. Res. Bull.* 7:1181-1190 (1972).

Aboba, "X-Ray Diffraction Study on the Amorphous and Crystalline Components in Bone Mineral", *Chem Abstracts*, vol. 91, No. 13 Abstrat No. 105935r, (1979).

Aboba et al., "Small Angle X-Ray Scattering Study on the Transformation of Amorphous Calcium Phosphate to Crystalline Apatite," *Chem. Abstracts*, vol. 91, No. 13, Abstract No. 105934q (1979).

Tung et al., "Hydrolysis of Dicalcium Phosphate Dihydrate in the Presence or Absence of Calcium Fluoride" Basic Biological Sciences *Dent. J. Res.* 64(1):2-5 Jan. 1985.

Tung et al., "An Intermediate State in Hydrolysis of Amorphous Calcium Phosphate", *Calcified Tissue International*, 783-790 (1983).

Tung, et al., "The Effects of Calcium Phosphate Solutions on Permeability of Dentin" *J. Dent. Res.*, 65 Abstract No. 167 (1986).

Tung et al., "Effects of Calcium Phosphate Solutions on Dentin Permeability", vol. 19, No. 8 *J of Endodontial* (1983).

Trautz, "Crystallographic Studies of Calcium Carbonate phosphate" Annals of the N.Y. Acad. Sci. 35, Article I 145-160 (1960).

Termine et al., "Calcium Phosphate in vitro", *Chem. Abstracts*, vol. 73, Abstract No. 126985a, (1970).

Yasue et al, "Synthesis and Characteristics of Amorphous Calcium Carbonate in Ethanol", *Fac. Sci Eng. Nihon Univ. Gypsum Lime*, 1985, 198 245-52 Japan.

Bowen et al., "Development of an Adhesive Bonding System", *Operative Dentistry*, Supplement 5, 1992, pp. 75-80.

Yu et al., "Self-Setting Hydroxyapatite Cement: A Novel Skeletal Drug-Delivery System for Antibiotic", *J Pharm. Sci.*, vol. 81, No. 6, Jun. 1992, pp. 529-531.

de Groot, "Ceramics of Calcium Phosphates: Preparation and Properties", *Bioceramics of Calcium Phosphate* pp. 99-114.

Posner et al. "Synthetic Amorphous Calcium Phsophate and Its Relation to Bone Mineral Structure", *Account of Chemical Research*, 8, 273 (1975).

International Search Report for PCT/US04/39819 mailed Nov. 30, 2005.

"Remineralisation of Natural Carious Lesions of Enamel In Vitro" Levine British Dental Journal pp. 132-134, 1974.

"Singular Points in the Chemistry of Teeth" Chow/Brown Journal of Dental Research AADR Abstract 1975 Abstract No. 120.

"Calcium Phosphate Binders for Hydroxylapatite Particles for Bone Repair" Hanker/Giammara/Chow Journal of Dental Research vol. 66 Abstract No. 1144, Mar. 1987.

"New Attachment Following the Use of a Novel Calcium Phosphate System" Lu/Siew/Robinson Journal of Dental Research vol. 67 Abstract No. 1913, Mar. 1988.

"Remineralization of Root Caries Lesion by a Calcium Phosphate Slurry" Schreiber/Takagi/Chow Journal of Dental Research vol. 67 Abstract No. 255, Aug. 20, 1974.

"Porous Hydroxylapatite-perichondrium Graft in Cricoid Reconstruction" Verwoerd/Adriaansen/Heul/Verwoerd-Verhoef Acta Oto-Laryngologica vol. 103 May-Jun. 1987 No. 5-6.

"Hydroxyapatite Cement—II. Obliteration and Reconstruction of the Cat Frontal Sinus" Friedman/Constantino/Jones/Chow/Pelzer/Sisson Archives of Otolaryngology-Head & Neck Surgery Apr. 1991 pp. 385-389.

"New Cement Makes Medical History—ADA Health Foundation Work Vital to Breakthrough" American Dental Association News vol. 24, No. 1 (3 pages), Jan. 24, 1993.

"Histopathological Reaction of a Calcium Phosphate Cement Root Canal Filler" Sugaware/Kusama/Nishimura/Nishiyama/Moro/Kudo/Chow/Takagi Journal of Hard Tissue Biology International The Japanese Society of Hard Tissue Research & Technology vol. 4 (1), Mar. 1995 pp. 1-7.

International Association for Dental Research, Dental Materials Group, New Orleans, LA, Abstracts, Mar. 1979 (14 pages).

International Association for Dental Research, Dental Material Group, Washington, DC, Abstracts, Mar. 1978 (10 pages).

\* cited by examiner

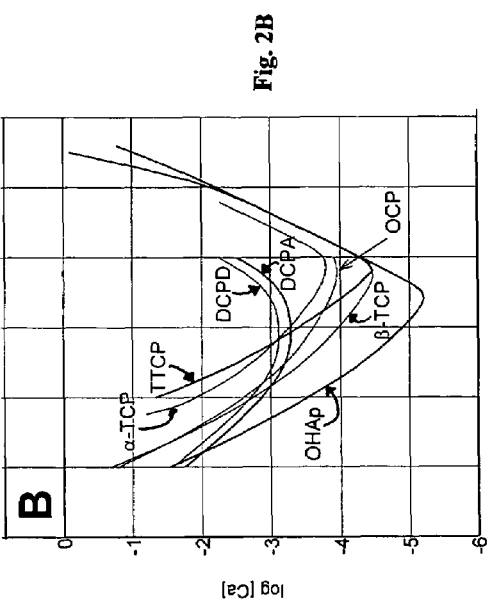
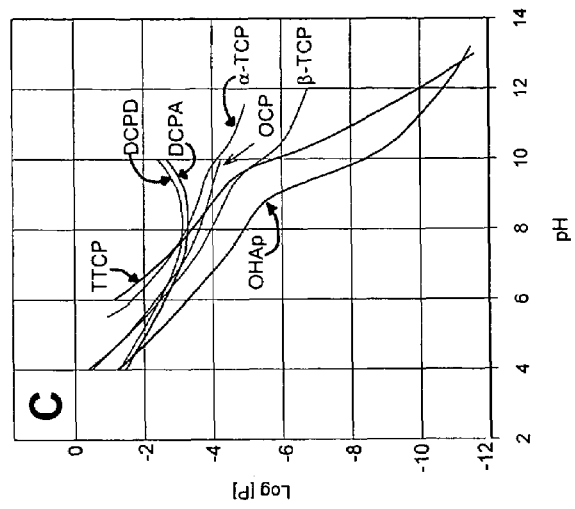
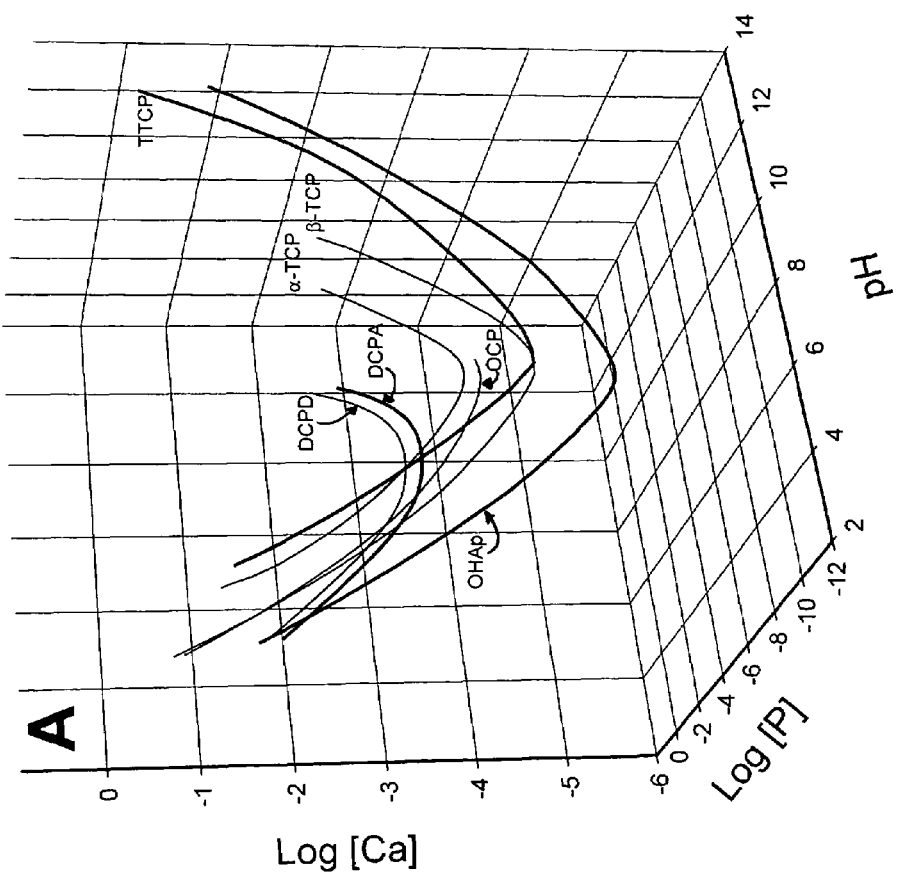

RAPID-HARDENING CALCIUM PHOSPHATE CEMENT COMPOSITIONS

CROSS-REFERENCE TO RELATED APPLICATIONS

This application is a continuation-in-part of U.S. application Ser. No. 10/057,554, filed Jan. 23, 2002, issued as U.S. Pat. No. 6,793,725, which claims the benefit of U.S. Provisional Patent Application Ser. No. 60/263,894, filed on Jan. 24, 2001. This application also is based on and claims the benefit of co-pending U.S. Provisional Patent Application Ser. No. 60/536,899, filed on Jan. 16, 2004. The parent specifications each are incorporated herein by reference in their entirety.

STATEMENT REGARDING FEDERALLY SPONSORED RESEARCH OR DEVELOPMENT

This development was supported in part by USPHS Research Grant DE11789 to the American Dental Association Foundation from the NIDCR. The United States or an agency thereof may have certain rights to the claimed invention.

BACKGROUND OF THE INVENTION

The various embodiments of the present invention relate to self-hardening calcium phosphate-containing and/or calcium-containing paste and cement compositions. The compositions may be used to form pastes for bone and tooth restoration and similar applications, where the paste will harden within a desired time after being delivered to a repair site.

Most conventional calcium phosphate cements are mixed with an aqueous solution immediately before application. In the clinical situation, the ability of the surgeon to properly mix the cement and then place the cement paste in the defect within the prescribed time is a crucial factor in achieving optimum results.

A self-hardening calcium phosphate cement (CPC), consisting of tetracalcium phosphate ($Ca_4(PO_4)_2O$, also referred to as "TTCP") and dicalcium phosphate anhydrous ($CaHPO_4$, also referred to as "DCPA"), has been shown in clinical studies to be efficacious for repairing bone defects. The hardening time of such conventional cements is as long as about 30 minutes with water, although hardening time can be shortened if a phosphate solution is used as the cement liquid. Hydroxyapatite ($Ca_5(PO_4)_3OH$, also referred to as "HA") is formed as the product. More recently, additional CPCs that do not contain TTCP, e.g., α-tricalcium phosphate (α-$Ca_3(PO_4)_2$, also referred to as "α-TCP") and $CaCO_3$ or DCPA and $Ca(OH)_2$, have also been developed. These cements may harden in about 10 minutes when a phosphate solution is used as the cement liquid. They also form hydroxyapatite as the final product.

A premixed CPC paste containing the TTCP and DCPA powders and glycerol as the cement liquid has been used for root canal filling and sealing by injection techniques. The cement paste was found to be stable in a syringe but hardened only after being delivered into the root canal where it became exposed to water from the surrounding tissues. Because the cement paste was injected into a confined area, there was little concern of disintegration of the paste due to washout. Although the premixed CPC was shown to have improved biocompatibility with periapical bone tissue than a number of conventional root canal filling or sealing materials, the premixed CPC-glycerol paste did not exhibit a good washout resistance when it was applied to an open wet field.

The patent literature also describes at least one class of calcium phosphate cement compositions which are precursors for the formation of hydroxyapatite and are biologically compatible, and have two unique properties that are not attainable in other calcium phosphate biomaterials: (1) self-hardening to form a mass with sufficient strength for many medical and dental applications, and (2) when implanted in bone, the cement resorbs slowly and is completely replaced by new bone formation with no loss in the volume or integrity of the tissue that receives the implant. See U.S. Pat. Nos. Re. 33,221 and Re 33,161 to Brown and Chow, which teach preparation of calcium phosphate remineralization compositions and of finely crystalline, non-ceramic, gradually resorbable hydroxyapatite cement based on the same calcium phosphate compositions.

The major components of the calcium phosphate remineralizing slurries, pastes and cements taught in U.S. Pat. Nos. Re. 33,221 and Re. 33,161 are preferably tetracalcium phosphate ($Ca_4(PO_4)_2O$), and at least one other sparingly soluble calcium phosphate, preferably dicalcium phosphate anhydrous ($CaHPO_4$), or dicalcium phosphate dihydrate ($CaHPO_4.2H_2O$). These react in an aqueous environment to form hydroxyapatite, the principal mineral in teeth and bones, as the final product. Because of the apatitic nature of the set cement, it is highly compatible with soft and hard tissues. This material, if applied intraoperatively as a paste, subsequently sets to a structurally stable implant composed of microporous hydroxyapatite.

A virtually identical calcium phosphate system which consists of tetracalcium phosphate (TTCP) and monocalcium phosphate anhydrous (MCPA) or its monohydrate form (MCPM) was described by Constantz et al. (U.S. Pat. Nos. 5,053,212 and 5,129,905). This cement system is believed to involve conversion of the MCPA to dicalcium phosphate which reacts with TTCP and forms hydroxyapatite, the major mineral component of teeth and bone, as the end product.

Constantz et al. U.S. Pat. Nos. 4,880,610 and 5,047,031 describe another cement system that consists of a mixture of solid phosphoric acid crystals, calcium carbonate, and calcium hydroxide as the cement powder and a 7.4 mol/L NaOH solution (4.5 g NaOH in 15 mL of water) as the cement liquid. Data on the physical and chemical properties (compressive strength, hardening time, nature of end product, pH of the cement fluid, heat of mixing etc.) of this cement have not been located in the patent or scientific literature.

BRIEF SUMMARY OF THE INVENTION

The various embodiments of the present invention comprise compositions and means for formulating calcium phosphate cement pastes that are stable in a package, resistant to washout and harden within a desired time after being delivered to a defect or implant site. Solutions are provided for promoting rapid setting of calcium phosphate cements upon blending of a solution with a calcium phosphate cement powder. The solutions and powders are stable and, when blended together, yield cement slurries having reduced hardening times.

Numerous solutions may be used in accordance with the present invention, however, the solutions each are capable of accelerating cement setting reactions upon blending with a calcium phosphate cement powder. In one embodiment, one or more calcium phosphate salts are present in a relatively reactive form, which accelerates cement setting reactions by acting as "seeds" to promote more rapid formation of hydroxyapatite and, thus, hardening of the cement. The solution can be an acidic calcium phosphate solution. The solution also can be a concentrated acidic solution. Dissolution of a calcium phosphate cement powder in such solutions results in precipitation of a calcium phosphate compound from solution. The precipitated compound is very reactive and enhances cement setting reactions to reduce cement hardening times.

In another embodiment, solutions of one or more salts that are not calcium salts can be mixed with calcium phosphate cement powders to increase the solution phosphate concentration and accelerate formation of hydroxyapatite. The solution can be a salt: (a) where the cationic component is not calcium and one or more of the anionic components form strong calcium complexes in solution, or (b) the cationic component is not calcium and one or more of the anionic components form insoluble salts with calcium. Dissolution of a calcium phosphate cement powder in the solution results in an increase in the phosphate concentration in the solution, which enhances cement setting reactions to reduce cement hardening times.

Another embodiment of the invention is a method of preparing a cement paste from a slurry for bone and tooth restoration. The method includes preparing a cement slurry from a solution and a calcium phosphate powder. The cement slurry hardens relatively rapidly into a formable paste that can be shaped before it hardens into a cement.

Still another embodiment of the invention is a method of repairing bone and tooth defects. The method includes blending the solutions and powders described above to provide a cement paste and filling a defect with the cement paste before it hardens substantially into a cement.

The invention further contemplates the improved calcium phosphate cement mixtures prepared by this method, the cement component(s) provided to the user in a pre-manufactured kit or delivery device, the methods of using the improved cement, and the biological implants made from the cement. A rapid-hardening industrial cement is also contemplated.

The invention includes a method for preparing calcium phosphate cement compositions, which self-harden substantially to hydroxyapatite at ambient temperature when in contact with an aqueous medium, the method including combining one or more calcium phosphate salts or calcium salts with a solution that is (1) an acidic calcium phosphate solution saturated with respect to more or more calcium phosphate compounds, (2) a concentrated acid solution, or (3) salt solutions with a cationic component other than calcium.

BRIEF DESCRIPTION OF THE DRAWINGS

FIG. 2A is a three-dimensional solubility phase diagram for the $Ca(OH)_2$—$H_3PO_4$—$H_2O$ system;

FIG. 2B is a projection of the diagram of FIG. 2A along the log[Ca] axis; and

FIG. 2C is a projection of the diagram of FIG. 2A along the log[P] axis.

DETAILED DESCRIPTION OF THE INVENTION

Figure 1:
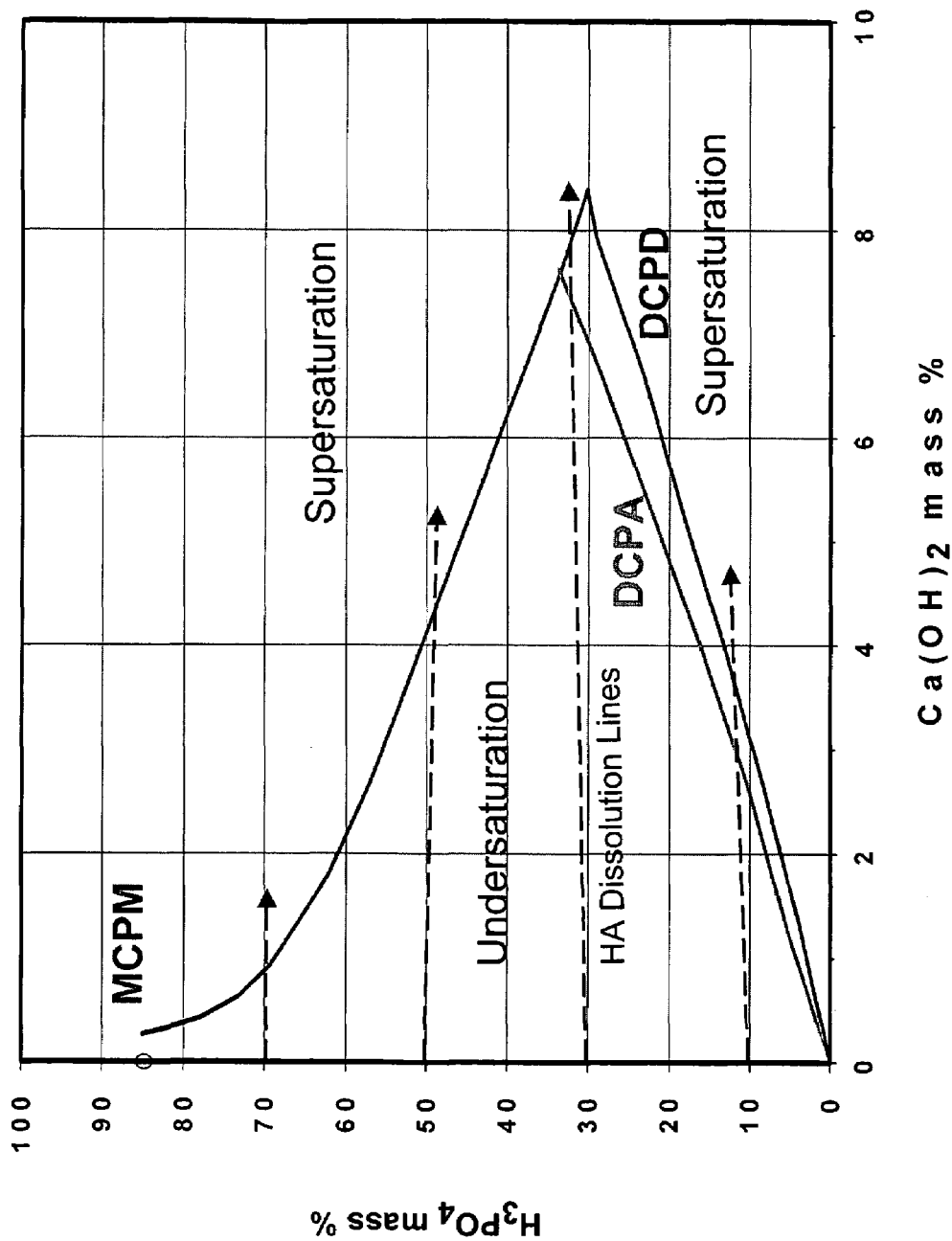
FIG. 1 shows the solubility phase diagram of the 3-component system, $Ca(OH)_2$—$H_3PO_4$—$H_2O$, showing the acidic and concentrated region of the phase diagram for the system.

Calcium phosphate cement compositions are prepared that yield a product that self-sets at ambient temperatures (i.e., room or body temperature) to hydroxyapatite (HA). The calcium phosphate cement compositions include a liquid solution and a powder composition. The use of certain calcium phosphate precursor cement slurry compositions results in a cement which sets reliably and quickly to HA. The setting rate can be adjusted for various end uses, and may be quite rapid if desired. The resulting hydroxyapatite cement is believed to be both biocompatible and resorbable (biodegradable) with bone replacement when in contact with living bone.

The calcium phosphate cement pastes can be used in bone graft and similar medical repair applications. The calcium phosphate cements can be mixed and/or shaped prior to delivery to a bone or tooth defect site. The pastes also can be provided in an injectable form for delivery to the bone or tooth defect site. The calcium phosphate cements harden relatively rapidly to form HA.

Formation of HA from the calcium phosphate cement slurries can be greatly accelerated by use of the inventive solutions that, when mixed with any one or more of a wide variety of calcium phosphate cement powders to form a slurry composition, results in: (1) an increase in phosphate concentration in the slurry composition and/or (2) an increase in the pH of the slurry composition. Without wishing to be bound by any theories, it is believed that the cement solutions provide effective means to accelerate the HA formation in the slurry systems because of the formation of intermediate compounds and/or calcium complexes either of which will precipitate more readily than HA at the lower solution pH. Such intermediate compounds and complexes are less soluble than HA at lower pH (below a pH of about 4), whereas HA is the least soluble phase at a pH of about 4 and greater.

FIG. 1 is a solubility phase diagram for the $Ca(OH)_2$—$H_3PO_4$—$H_2O$, in which both the solid phase and the saturated solution contain only those ions or non-charged species that are derived from the three components, $Ca(OH)_2$, $H_3PO_4$, and $H_2O$. FIG. 1 shows the acidic and concentrated region of the phase diagram. Each solid line in the diagram is referred to as a solubility isotherm and represents the compositions (expressed in terms of $H_3PO_4$ mass % and $Ca(OH)_2$ mass %) of a series of solutions that are saturated with respect to the indicated solid, i.e., MCPM, DCPD, or DCPA. The point where two isotherms meet is referred to as a singular point, where the solution is saturated with respect to both solids. In FIG. 1, those solution compositions that are to the left of an isotherm are super saturated with respect to the solid, and those to the right of the isotherm are under saturated. The vertical axis represents $H_3PO_4$ solution concentrations.

The dashed lines are used to illustrate the changing solution compositions that occur when HA dissolves into $H_3PO_4$ solutions of different concentrations. By way of example, it can be seen that when HA dissolves into a 10% $H_3PO_4$ solution, the dissolution line will first cross the DCPA isotherm, at which point the solution becomes saturated with respect to DCPA. Being an anhydrous salt, DCPA does not always readily precipitate, allowing the HA dissolution line to cross the DCPD isotherm. Further HA dissolution will lead to DCPD precipitation. Similarly, when HA dissolves into a 30% $H_3PO_4$ solution, the dissolution line will cross the DCPA isotherm and then the MCPM isotherm, resulting in precipitation of DCPA or MCPM or both. In contrast, dissolution of HA into a 50% or 70% $H_3PO_4$ solution will lead to MCPM precipitation only. The above illustrates how the phase diagram of FIG. 1 can be used to predict the phases that would form as a result of dissolution of HA in any solution composition covered in the diagram. A similar analysis is possible with any other calcium phosphate, e.g., tetracalcium phosphate, tricalcium phosphate, dicalcium phosphate, etc., as the dissolving compound.

The lower left corner of the phase diagram, sometimes referred to as the "water corner," represents the region of the solubility phase diagram for the $Ca(OH)_2$—$H_3PO_4$—$H_2O$ system where the pH is about 4 or above. Because the Ca and P concentrations of the solutions for this region are much lower than those in the acidic region, another solubility phase diagram that employs logarithmic scales is used to illustrate the relative stability of the various calcium phosphate phases, which is the major driving force for phase transformation reactions, as a function of pH. FIG. 2A is a three-dimensional solubility phase diagram showing the solubility isotherms of the various calcium phosphate phases that are stable in the pH range of 4 to 12. FIGS. 2B and 2C illustrate the projections of the three-dimensional diagram along the log[P] and log[Ca] axes, respectively. In FIGS. 2B and 2C, those solutions that are below an isotherm are undersaturated with respect to the indicated solid phase and those above the isotherms are supersaturated with respect to the indicated solid phase.

It can be seen in the figures that among all calcium phosphate salts, HA is the least soluble in a wide range of solution pHs, ranging approximately from 4.5 to 14. Thus, within this pH range, any other calcium phosphate or mixture of calcium phosphates has the tendency to dissolve and reprecipitate as HA. However, in general the rate of HA formation is very slow such that a slurry of DCPD, DCPA, octacalcium phosphate ($Ca_8H_2(PO_4)_6.5H_2O$, or "OCP"), amorphous calcium phosphate ($Ca_3(PO_4)_2$, or "ACP"), α-tricalcium phosphate (α-$Ca_3(PO_4)_2$, or "α-TCP"), β-tricalcium phosphate (β-$Ca_3(PO_4)_2$, or "β-TCP"), or a mixture of these salts does not produce a setting cement or act as an effective remineralizing agent.

Acceleration of HA formation can be achieved using the present solutions with calcium phosphate cement powders because of increased phosphate concentration and/or increased solution pH. The intermediate compounds will form initially. As the cement setting reactions proceed, the solution pH increases and the compounds will begin to dissolve. The formation of HA and dissolution of the more soluble intermediate compounds are responsible for the hardening of the cement. Preferably, the pH of the prepared cement paste systems increases with time to be in the range of approximately 4.5 to 14, the range in which HA is the most stable phase. With these conditions, more rapid HA formation and subsequent cementation can occur.

A variety of solutions can be used in accordance with the invention. Generally, the solutions can be grouped based on the mechanism by which the solutions accelerate cement setting reactions.

In one embodiment, one or more calcium phosphate salts in the cement solutions are generally very reactive with respect to hydroxyapatite formation, thereby promoting more rapid formation of hydroxyapatite and reducing hardening time of the cements. Without wishing to be bound by any theories, it is believed that the calcium phosphate salts act as "seeds" that promote hydroxyapatite formation. That is, the calcium phosphate salts precipitate to form reactive particles that provide the foundation from which hydroxyapatite forms. At least initially, when the solution is at a lower pH, the calcium phosphate particles are not highly soluble in the non-aqueous solutions or water. The phosphate concentration of the paste is not expected to increase by any significant amount if exposed to an aqueous environment. The calcium phosphate "seeds" provide a template for growth of hydroxyapatite crystal growth, which enhances the rate of formation of hydroxyapatite and provides more rapid hardening of the cement.

In a first group of solutions, the solutions are acidic calcium phosphate solutions that are saturated with respect to monocalcium phosphate monohydrate ($Ca(H_2PO_4)_2.H_2O$, or "MCPM") or monocalcium phosphate anhydrous ($Ca(H_2PO_4)_2$, or "MCPA"). These solutions generally have a pH between about 0 to about 1.9, a $Ca(OH)_2$ content from about 0.3% to about 8.5%, and a $H_3PO_4$ content of about 30% to about 80% (see the solid curve for MCPM in FIG. 1). They are not supersaturated with respect to other calcium phosphate phases, and are stable as a result. When the solution is mixed with a calcium phosphate cement powder, the powder dissolves and the solution pH increases. As described previously, dissolution of the cement components leads to increases in pH and calcium and phosphate concentrations. The solution will become supersaturated with respect to MCPM or MCPA, and MCPM or MCPA will precipitate from the respective solutions. The MCPM and MCPA formed in situ are highly reactive. The precipitate acts as "seeds" that accelerate cement setting reactions and reduce cement hardening time.

In a second group of solutions, the solutions are acidic calcium phosphate solutions that are saturated with respect to dicalcium phosphate dihydrate ($CaHPO_4.2H_2O$, or "DCPD") or dicalcium phosphate anhydrous ($CaHPO_4$, or "DCPA"). These solutions generally have a pH between about 1.9 to about 4.3, a $Ca(OH)_2$ content from about 0.05% to about 8.5%, and a $H_3PO_4$ content of about 0.1% to about 30% (see the solid curves for DCPA and DCPD in FIG. 1). The DCPA saturated solutions are not supersaturated with respect to other calcium phosphate phases, and are stable as a result. The DCPD saturated solutions are not supersaturated with respect to other calcium phosphate phases except DCPA, but DCPA does not readily precipitate from these solutions. The solutions thus are expected to be stable for longer periods, e.g., about 1 year or more. When the solution is mixed with a calcium phosphate cement powder, the powder dissolves and the solution pH and calcium and phosphate concentrations increase. As the solution becomes supersaturated with respect to DCPD or DCPA, DCPD or DCPA will precipitate from the respective solutions. The DCPD and DCPA formed in situ are highly reactive. The precipitate acts as "seeds" that accelerate cement setting reactions and reduce cement hardening time.

In third group of solutions, the solutions are concentrated acid solutions. Suitable solutions include hydrochloric acid (HCl), nitric acid ($HNO_3$), phosphoric acid ($H_3PO_4$), glycerolphosphoric acid (($HOCH_2)_2CHOPO(OH)_2$), and acetic acid ($CH_3COOH$). The pH of these solutions is highly acidic. When the solution is mixed with a calcium phosphate cement powder, the powder dissolves. MCPM, MCPA, DCPD, DCPA and combinations thereof will precipitate according to the acid strength and concentration. That is, MCPM and MCPA are expected to precipitate in a stronger acid solution, and DCPD and DCPA are expected to precipitate in a weaker acid solution. The MCPM, MCPA, DCPD and DCPA formed in situ are highly reactive. The precipitate acts as "seeds" that accelerate cement setting reactions and reduce cement hardening time.

Solution concentrations should be sufficiently high enough so that MCPM, MCPA, DCPD, and/or DCPA will form when using solutions of the third group. For example, the $H_3PO_4$ concentration preferably is at least about 0.015 M. The minimum concentrations of other acid solutions in the third group are likely somewhat higher because they do not contain phosphate ions. It is anticipated that the effectiveness of the acid solutions in providing a rapidly setting cement generally will decrease with decreasing acid concentration. Thus, for a given acid solution, it is anticipated that there will be a particular concentration range that will provide a desired setting time.

In another embodiment, the solutions are solutions of a salt where the cationic component(s) is not calcium and one or more of the anionic component(s) form strong calcium complexes in the solution. Suitable solutions of this type include sodium acetate, sodium lactate, sodium cacodylate and the like. Alternatively, the solutions are solutions of a salt where the cationic component(s) is not calcium and one or more of the anionic components form insoluble salts with calcium. Suitable solutions of this type include sodium fluoride, potassium oxalate, sodium sulfate and the like. When solutions of either of these types are mixed with a calcium phosphate cement powder, the concentration of the free, or uncombined, form of the anionic component(s) in the solution and the concentration of the free calcium in the solution decrease, as a result at least in part, of complex formation or precipitation. Correspondingly, the concentration of phosphate in the solution increases to maintain the electroneutrality in the solution. An increased concentration of phosphate accelerates cement setting reactions. The pH of the solution may vary but should promote at least some degree of solubility of the calcium phosphate powders. Preferably, the pH is selected to promote a higher degree of powder solubility.

The cement compositions also include one or more cement powders. Powders that can be mixed with any of the above solutions to yield a rapid-hardening cement include (1) one or more calcium phosphate salts, or (2) one or more calcium phosphate salts and one or more calcium salts. Suitable calcium phosphate salts include (in the order of increasing calcium to phosphate ratio) but are not limited to MCPM, MCPA, DCPD, DCPA, OCP, ACP, α-TCP, β-TCP, HA, carbonated HA, calcium-deficient HA, poorly crystalline HA, tetracalcium phosphate (TTCP), and precipitated or high temperature products that are homogeneous mixtures of one or more of the above salts. Suitable calcium salts are sparingly to moderately soluble calcium-containing compounds, which include but are not limited to calcium oxide (CaO), calcium hydroxide ($Ca(OH)_2$), calcium carbonate ($CaCO_3$), calcium glycerophosphate, calcium gluconate, calcium lactate, and calcium sulfate.

The particle sizes of the powders preferably are in the range of between about 0.05 µm to about 500 µm, more preferably between about 1 µm to about 100 µm. The crystallinity of the powders can range from very low (amorphous) to high.

The compositions also may include one or more additives to enhance the properties of the compositions, such as when used in clinical applications. Additives may include medicaments, filler materials, crystal adjustors, viscosity modifiers, gelling agents, pore forming agents, resorbable and nonresorbable fibers and meshes, osteoinductive factors, bone morphogenic proteins, other proteins, and combinations thereof.

The cement compositions may include one or more non-toxic gelling agents to enhance paste cohesiveness and washout resistance. The gelling agent may include hydroxypropyl methylcellulose, carboxylmethylcellulose, starch, proteoglycans, glycoproteins, chitosan and chitosan derivatives, collagen, gum, gelatin, and alginate, and combinations thereof. Use of a gelling agent can increase the rate of hardening of the cement.

Filler materials can be added in amounts effective for enhancing the strength of the cement. Suitable filler materials include but are not limited to non-toxic biocompatible natural or synthetic polymers, non-toxic biocompatible metals, and other non-toxic biocompatible organic and inorganic materials. Fillers can be in the form of granules, fibers, rods, sheets, grids or other suitable forms.

Pore forming agents can be selected to form pores having diameters effective to result in vascularization of tissue that infiltrates the composition. Preferably, the pore diameter ranges between about 30 µm to about 500 µm, or more preferably, between about 100 µm to about 350 µm. The pore forming agents are selected from materials that are sufficiently insoluble in the cement pastes to enable incorporation of the pore forming agents into the hardened cement but that are sufficiently soluble to be substantially removed by dissolution in physiological fluids or resorbed by actions of cells after implantation. Alternatively, the agents can be removed after hardening of the cement using solvents or heating. Suitable solvents include water, ethanol, acetone, ether, and any other organic solvent in which the pore forming agent dissolves. If heated, the temperature should be sufficiently high enough to remove the pore forming agent by decomposition, sublimation, evaporation, combustion, etc. Preferably, the cement is heated to a temperature range of from about 100° C. to about 1200° C., although other heating temperatures also may be employed. The pore forming agents may include sugar, sodium bicarbonate and phosphate salts. Phosphate salts are effective pore forming agents because the use of concentrated phosphate solutions in the cement makes them relatively insoluble in the cement. A particularly useful phosphate salt is disodium phosphate.

Preferably, the precipitated calcium phosphate seeds that form in the slurry compositions are an acidic calcium phosphate compound. Such compounds include, inter alia, DCPA, DCPD, MCPA, MCPM, ACP and HA. Preferably, the compound is DCPD or MCPM, and combinations thereof.

The particle size of the calcium phosphate seeds can vary. By way of example, nanometer-size particles of calcium phosphate compounds will promote hydroxyapatite formation.

The compositions may be employed as rapid-hardening cement pastes in a variety of medical and dental procedures for repairing or restoring missing or defective bone or tooth tissue. The cement pastes may be applied to the defect site using any suitable methods, including injecting with a syringe or depositing with a spatula, and also molded or sculpted in vivo as desired. When the solutions are mixed with the cement powders, the resulting slurry compositions will harden relatively rapidly.

For most clinical applications, a cement hardening time of more than 60 minutes is too long. Additionally, if the cement sets too rapidly, the time to sculpt the paste into the desired shape and deposit it at the defect site may not be sufficient. The cement composition in accordance with the various embodiments of the present invention will have a hardening, or setting, time of no more than about 35 minutes, preferably no more than 20 minutes and even more preferably between about 5 to about 15 minutes.

EXAMPLES

The following examples further illustrate preferred embodiments of the present invention but are not be construed as in any way limiting the scope of the present invention as set forth in the appended claims.

Various cement paste systems were prepared. Setting times and other properties of the pastes were evaluated.

Preparation of Cement Powders: TTCP, α-TCP and β-TCP are prepared using conventional methods known to those of skill in the art and described below. DCPA, DCPD, HA, $CaCO_3$, and $Ca(OH)_2$ are commercially available reagent grade chemicals, such as available from J.T. Baker Chemical Co., Phillipsburg, N.J.

TTCP is prepared by heating an equimolar mixture of commercially obtained DCPA (Baker Analytical Reagents, J.T. Baker Chemical Co., Phillipsburg, N.J.) and $CaCO_3$ (J.T. Baker Chemical Co.) at about 1500° C. for about 6 hours in a furnace and quenched at room temperature. Alternatively, appropriate amounts of DCPA and $CaCO_3$ are used to obtain a Ca/P molar ratio of between about 1.8 to about 2.2 if it is desired to have TTCP in the final product and minor amounts of other phases including α-TCP, HA, and CaO. α-TCP is prepared by heating a mixture that contains about 2 mol of DCPA and about 1 mol of $CaCO_3$ to about 1500° C. for about 6 hours and then quenching in air. Alternatively, appropriate amounts of DCPA and $CaCO_3$ are used to obtain a Ca/P molar ratio of between about 1.5 to about 1.7 if it is desired to have α-TCP in the final product and various amounts of HA. β-TCP is similarly prepared, except that the mixture is heated to about 1200° C. and allowed to cool to room temperature in the furnace. The powders are ground individually in a planetary ball mill in cyclohexane, ethanol, or without a liquid to obtain the median particle sizes indicated in the tables below. When not indicated in the tables, the median particle size of TTCP is about 17 μm, α-TCP is about 5 μm, DCPA is about 1 μm, $CaCO_3$ is about 4 μm, and $Ca(OH)_2$ is about 2 μm.

Preparation of Solutions: The various cement solutions are prepared by dissolving appropriate amounts of the indicated compounds in distilled water to obtain the concentrations indicated below. Solutions of Examples 1 and 2 are prepared using conventional methods known to those of skill in the art and described in the literature. All other solutions are prepared by dissolving appropriate amounts of the indicated compounds in distilled water to obtain the concentrations indicated in the tables below.

Test Methods: The selected solutions and powders are blended at a mass ratio of between about 0.25 to about 0.5 to form a smooth paste composition. The paste is placed in a mold, and the mold is maintained at a temperature of about 37° C. and 100% humidity to simulate expected conditions at a defect site.

Cement setting time is measured with a Gilmore needle apparatus using a heavy Gilmore needle (453.5 g load, 1.06 mm diameter). The cement is considered set when the needle fails to leave a visible indentation when placed over the surface of the cement. Compressive strength measurements are performed on 24-hour, wet specimens using a computer-controlled Universal Testing Machine (Instron, United Calibration Corp., Garden Grove, Calif.). Powder X-ray diffraction analysis (Rigaku, Danvers, Mass., USA) is used to identify the phases that are present in 24-hour cement samples.

Example 1

In this example, a MCPM-forming solution having a pH of about 1, a calcium concentration of about 0.66 M, and a phosphorus concentration of about 7.6 M is used as the cement liquid. This solution is prepared by stirring an excess amount of MCPM in a solution of $H_3PO_4$ (about 6.3 M) until equilibrium, followed by filtration.

The powders also are mixed with water to provide comparative setting times.

TABLE 1

| Powder | Setting time (min): water | Setting time (min): MCPM solution | Products Formed (after 24 hours) |
|---|---|---|---|
| TTCP and DCPA | 30 | <12 | 90% HA |
| α-TCP and DCPA | 30 | <15 | 90% HA |
| DCPA and $Ca(OH)_2$ | does not set | <20 | |
| TTCP(Ca: P = 1.9)(17 μm) | does not set | <10 | |
| α-TCP (17 μm) | does not set | <30 | 20% HA |
| α-TCP (5 μm) | does not set | <40 | |

This example illustrates that the inventive solutions promote relatively rapid hardening and that the cements do not harden as a result of the cement powders contacting an aqueous solution (water alone).

Example 2

In this example, a DCPD-forming solution having a pH of about 2.1, a calcium concentration of about 1.5 M and a phosphorus concentration of about 4.4 M is used as the cement liquid. The solution is prepared by stirring an excess amount of DCPD in a solution of $H_3PO_4$ (about 2.9 M) until equilibrium, followed by filtration. The powders also are mixed with water to provide comparative setting times.

TABLE 2

| Powder | Setting Time (min): water | Setting Time (min): DCPD solution | Compressive Strength (MPa) | Products Formed (after 24 hours) |
|---|---|---|---|---|
| TTCP and DCPA | 30 | <10 | | 80% HA |
| α-TCP and $CaCO_3$ | does not set | <20 | | 100% HA |
| DCPA and $Ca(OH)_2$ | does not set | <25 | | 50% HA |
| TTCP(Ca: P = 2) (17 μm) | does not set | 30 | | 80% HA |
| TTCP(Ca: P = 2) (5 μm) | does not set | <40 | 9.2 (n = 3) | 98% HA |
| TTCP(Ca: P = 1.95) (20 μm) | does not set | <25 | | 80-90% HA |
| TTCP(Ca: P = 1.9) (15 μm) | does not set | 30 | 18.9 | 80% HA |
| TTCP(Ca: P = 1.9) (5 μm) | does not set | <15 | 10.4 (n = 2) | poorly HA |
| TTCP(Ca: P = 1.67) (5 μm) | does not set | <13 | 21.7 (n = 3) | poorly HA |
| α-TCP (5 μm) | does not set | <25 | 22.5 (n = 3) | 80% HA, 20% DCPD |
| β-TCP (17 μm) | does not set | 28 | | |

TABLE 2-continued

| Powder | Setting Time (min): water | Setting Time (min): DCPD solution | Compressive Strength (MPa) | Products Formed (after 24 hours) |
|---|---|---|---|---|
| β-TCP (5 μm) | does not set | 27 | | 0% HA, 20% DCPD |
| HA (from Fisher) | does not set | 20 | | 30% DCPD |

This example illustrates that the inventive solutions promote relatively rapid hardening and that the cements do not harden as a result of the cement powders contacting an aqueous solution (water alone).

Example 3

In this example, concentrated acid solutions are used as the cement liquid. The powders also are mixed with water to provide comparative setting times.

TABLE 3

| Powder | Liquid | Setting time (min) | Products formed (after 24 hours) |
|---|---|---|---|
| TTCP and DCPA | water | 30 | 90% HA |
| TTCP and DCPA | 0.016 N HCl | <25 | 95% poorly HA |
| TTCP and DCPA | 0.063 N HCl | <20 | |
| TTCP and DCPA | 1.0 N HCl | <15 | |
| TTCP and DCPA | 0.016 N HNO$_3$ | <25 | 95% poorly HA |
| TTCP and DCPA | 0.032 N HNO$_3$ | 15 | 95% poorly HA |
| TTCP and DCPA | 1.0 N HNO$_3$ | <15 | 95% poorly HA |
| TTCP and DCPA | 0.004 M H$_3$PO$_4$ | 25 | 90% HA |
| TTCP and DCPA | 0.008 M H$_3$PO$_4$ | 25 | 90% HA |
| TTCP and DCPA | 0.016 M H$_3$PO$_4$ | 22 | 90% HA |
| TTCP and DCPA | 0.078 M H$_3$PO$_4$ | 20 | 90% HA |
| TTCP and DCPA | 1.0 M H$_3$PO$_4$ | 15 | 90% HA |
| TTCP and DCPA | 0.016 M acetic acid | <25 | 97% HA |
| TTCP and DCPA | 0.063 M acetic acid | <20 | HA |
| TTCP and DCPA | 0.01 M acetic acid | <17 | HA |
| TTCP and DCPA | 1M acetic acid | <17 | 97% HA |
| TTCP and DCPA | 0.016 M lactic acid | 25 | 90% HA |
| TTCP and DCPA | 0.063 M lactic acid | 20 | 90% HA |
| TTCP and DCPA | 1M lactic acid | 20 | 90% HA |
| TTCP and DCPA | 3 M glycerol phosphoric acid | <2 | |
| TTCP and DCPA | 0.75 M glycerol phosphoric acid | 5 | |
| TTCP and DCPA | 0.19 M glycerol phosphoric acid | 10 | |
| TTCP and DCPA | 0.05 M glycerol phosphoric acid | 25 | |
| DCPA and Ca(OH)$_2$ | water | does not set | |
| DCPA and Ca(OH)$_2$ | 1N HNO$_3$ | 27 | 65% HA |
| DCPA and Ca(OH)$_2$ | 1M H$_3$PO$_4$ | <60 | 35% HA |
| α-TCP and CaCO$_3$ | water | does not set | |
| α-TCP and CaCO$_3$ | 1N HCl | 25 | 100% poorly HA |
| α-TCP and CaCO$_3$ | 1M H$_3$PO$_4$ | <12 | 60% HA, 40% DCPA |
| α-TCP and DCPA | water | 35 | |
| α-TCP and DCPA | 1N HCl | <20 | 70% poorly HA |
| α-TCP and DCPA | 1M H$_3$PO$_4$ | 20 | 30% HA, 20% DCPD, 50% DCPA |
| α-TCP (5 μm) | water | does not set | |
| α-TCP (5 μm) | 1N HNO$_3$ | <15 | 100% poorly HA |
| α-TCP (5 μm) | 1N HCl | <20 | 100% poorly HA |
| α-TCP (5 μm) | 1M H$_3$PO$_4$ | <20 | 60% HA, 40% DCPD |
| TTCP(Ca: P = 1.9)(5 μm) | water | does not set | |
| TTCP(Ca: P = 1.9)(5 μm) | 1M H$_3$PO$_4$ | <25 | 100% poorly HA |
| β-TCP (5 μm) | water | does not set | |
| β-TCP (5 μm) | 1M H$_3$PO$_4$ | 70 | |

This example illustrates that the inventive solutions promote relatively rapid hardening and that the cements do not harden as a result of the cement powders contacting an aqueous solution (water alone).

Example 4

In this example, salt solutions that form calcium-complexes or insoluble calcium salts are used as the cement liquid. The powders also are mixed with water to provide comparative setting times.

TABLE 4

| Powder | Liquid | Setting time (min) | Products formed (after 24 hours) |
|---|---|---|---|
| TTCP and DCPA | water | 30 | 90% HA |
| TTCP and DCPA | 2% NaF | 10 | 70% HA |
| TTCP and DCPA | 1 M NaF | 13 | 95% HA |
| TCCP and DCPA | 1 M KF | 7 | 95% HA |
| TTCP and DCPA | 1 M Na acetate | 13 | 60% HA |
| TTCP and DCPA | 1 M $C_2K_2O_4$ | 13 | 85% HA |
| TTCP and DCPA | 0.016 M $Na_2SO_4$ | <25 | 85% HA |
| TTCP and DCPA | 0.063 M $Na_2SO_4$ | 17 | 85% HA |
| TTCP and DCPA | 1 M $Na_2SO_4$ | 12 | 85% HA |
| TTCP and DCPA | 1 M Na cacodylate | 20 | |
| DCPA and $Ca(OH)_2$ | water | does not set | |
| DCPA and $Ca(OH)_2$ | 2% NaF | <15 | 100% poorly HA |
| DCPA and $Ca(OH)_2$ | 1M NaF | <13 | 100% poorly HA |
| DCPA and $Ca(OH)_2$ | 1M KF | <7 | 100% poorly HA |
| DCPA and $Ca(OH)_2$ | 1M $Na_2SO_4$ | <20 | 100% poorly HA |
| DCPA and $Ca(OH)_2$ | 1M Na cacodylate | 23 | 65% HA |
| DCPA and $Ca(OH)_2$ | 1M $C_2K_2O_4$ | <15 | 100% poorly HA |
| α-TCP and DCPA | 1M NaF | 10 | 60% HA |
| α-TCP and DCPA | 1M Na acetate | 30 | 60% HA, 40% DCPA |
| TTCP(Ca: P = 1.9) (5 μm) | water | does not set | |
| TTCP(Ca: P = 1.9) (5 μm) | 1.0 M NaF | 50 | 100% poorly HA |
| TTCP(Ca: P = 1.9) (5 μm) | 1.0 M $C_2K_2O_4$ | 15 | 100% poorly HA |
| α-TCP (5 μm) | water | does not set | |
| α-TCP (5 μm) | 1.0 M NaF | 90 | 100% poorly HA |
| α-TCP (5 μm) | 1.0 M Na acetate | 80 | 100% poorly HA |
| α-TCP (5 μm) | 1.0 M $C_2K_2O_4$ | 17 | 100% poorly HA |
| α-TCP (5 μm) | 1.0 M $Na_2SO_4$ | 35 | 100% poorly HA |

This example illustrates that the inventive solutions promote relatively rapid hardening and that the cements do not harden as a result of the cement powders contacting an aqueous solution (water alone).

Example 5

This example illustrates the effects of the solutions of Example 4 on the phosphate concentration of cement liquid during setting.

Method and Materials: Approximately 0.4 g of an equimolar TTCP (median size=17 μm) and DCPA (1 μm) mixture is mixed with 1 mL of the various test solutions for the times set forth in Table 5. Phosphate concentration in the solution phase is determined.

TABLE 5

| Liquid | Mixing time (min) | Phosphate conc. |
|---|---|---|
| Water | 3 | 0.61 |
| Water | 15 | 0.40 |
| 1.0 M NaF | 3 | 296 |
| 1.0 M NaF | 15 | 330 |
| 1.0 M $Na_2SO_4$ | 3 | 6 |
| 1.0 M Na acetate | 3 | 6 |

When the solutions of Example 4 are used as the cement solutions, the phosphate concentrations in solution are significantly higher than when water is used. These results provide further support the mechanism of accelerated setting reaction postulated above when the solutions of Example 4 are used.

Although particular embodiments of the present invention have been described and illustrated, it should be understood that the invention is not limited thereto as modifications may be made by persons skilled in the art. The present application contemplates any and all modifications that fall within the spirit and scope of the underlying invention disclosed herein.

What is claimed is:

1. A composition of matter for dental restoration and bone implants and restoration comprising:
    a powdered calcium compound including one or more calcium phosphate salts selected from the group consisting of monocalcium phosphate monohydrate, monocalcium phosphate anhydrous, dicalcium phosphate anhydrous, dicalcium phosphate dihydrate, octacalcium phosphate, α-tricalcium phosphate, β-tricalcium phosphate, amorphous calcium phosphate, hydroxyapatite, tetracalcium phosphate and combinations thereof; and
    an acidic calcium phosphate solution saturated with respect to monocalcium phosphate monohydrate, monocalcium phosphate anhydrous or combinations thereof.

2. The composition of claim 1 wherein the powdered calcium compound includes one or more calcium salts selected from the group consisting of calcium oxide, calcium hydroxide, calcium carbonate, calcium glycerophosphate, calcium gluconate, calcium sulfate, calcium lactate and combinations thereof.

3. The composition of claim 1 including one or more additives selected from the group consisting of medicaments, filler materials, crystal adjustors, viscosity modifiers, gelling agents, pore forming agents, resorbable and nonresorbable fibers and meshes, osteoinductive factors, bone morphogenic proteins, and other proteins.

4. The composition of claim 3, wherein the one or more additives is a gelling agent selected from the group consisting of hydroxypropyl methyl cellulose, carboxymethyl cellulose, chitosan, chitosan derivatives, collagen, gum, gelatin, and alginate, and combinations thereof.

5. The composition of claim 3, wherein the one or more additives is a filler material.

6. The composition of claim 3, wherein the one or more additives is a pore forming agent.

7. The composition of claim 1, wherein the pH of the acidic composition is initially between about 0 to about 1.9.

8. A composition of matter for dental restoration and bone implants and restoration comprising:
   a powdered calcium compound including one or more calcium phosphate salts selected from the group consisting of monocalcium phosphate monohydrate, monocalcium phosphate anhydrous, dicalcium phosphate anhydrous, dicalcium phosphate dihydrate, octacalcium phosphate, α-tricalcium phosphate, β-tricalcium phosphate, amorphous calcium phosphate, hydroxyapatite, tetracalcium phosphate and combinations thereof; and
   an acidic calcium phosphate solution saturated with respect to dicalcium phosphate dihydrate, dicalcium phosphate anhydrous and combinations thereof.

9. The composition of claim 8 wherein the powdered calcium compound includes one or more calcium salts selected from the group consisting of calcium oxide, calcium hydroxide, calcium carbonate, calcium glycerophosphate, calcium gluconate, calcium sulfate, calcium lactate and combinations thereof.

10. The composition of claim 8 including one or more additives selected from the group consisting of medicaments, filler materials, crystal adjustors, viscosity modifiers, gelling agents, pore forming agents, resorbable and nonresorbable fibers and meshes, osteoinductive factors, bone morphogenic proteins, and other proteins.

11. The composition of claim 10, wherein the one or more additives is a gelling agent selected from the group consisting of hydroxypropyl methyl cellulose, carboxymethyl cellulose, chitosan, chitosan derivatives, collagen, gum, gelatin, and alginate, and combinations thereof.

12. The composition of claim 10, wherein the one or more additives is a filler material.

13. The composition of claim 10, wherein the one or more additives is a pore forming agent.

14. The composition of claim 1, wherein the pH of the acidic composition is initially between about 1.9 to about 4.3.

15. A method of repairing bone and tooth defects comprising:
   (a) preparing the composition of any one of claims 1 and 8; and
   (b) filling the defect with the composition prior to hardening of the composition.

16. A calcium phosphate bone cement that self-hardens at ambient temperature and is resorbable when implanted in contact with living bone comprising the composition of any one of claims 1 and 8.

* * * * *